United States Patent
Griesbach, III

(10) Patent No.: US 9,433,770 B2
(45) Date of Patent: Sep. 6, 2016

(54) MEDICAL CONNECTOR WITH SPANNING ARMS

(71) Applicant: AVENT, INC., Alpharetta, GA (US)

(72) Inventor: Henry L. Griesbach, III, Atlanta, GA (US)

(73) Assignee: Avent, Inc., Alpharetta, GA (US)

( * ) Notice: Subject to any disclaimer, the term of this patent is extended or adjusted under 35 U.S.C. 154(b) by 745 days.

(21) Appl. No.: 13/729,294

(22) Filed: Dec. 28, 2012

(65) Prior Publication Data

US 2014/0188087 A1    Jul. 3, 2014

(51) Int. Cl.
    *A61M 39/10*      (2006.01)
    *A61J 15/00*      (2006.01)

(52) U.S. Cl.
    CPC ....... *A61M 39/1011* (2013.01); *A61J 15/0015* (2013.01); *A61J 15/0026* (2013.01); *A61J 15/0065* (2013.01); *A61M 39/1055* (2013.01); *A61M 2039/1027* (2013.01)

(58) Field of Classification Search
CPC ........... A61M 39/1011; A61M 25/02; A61M 39/0247; A61M 2025/0246; A61M 2025/028; A61M 39/12; A61M 2039/1077; A61M 2039/267; A61M 2039/1016; A61M 2039/1027; A61M 39/10; A61J 15/0026; A61J 15/0053; A61J 15/0057; A61J 15/0065
See application file for complete search history.

(56) References Cited

U.S. PATENT DOCUMENTS

| | | | | |
|---|---|---|---|---|
| 5,549,657 A * | 8/1996 | Stern | ................... | A61J 15/0015 604/246 |
| 6,019,746 A | 2/2000 | Picha et al. | | |
| 6,458,106 B1 * | 10/2002 | Meier | ................. | A61J 15/0015 604/175 |
| 6,736,797 B1 * | 5/2004 | Larsen | .................. | A61M 5/158 604/167.05 |
| 6,923,791 B2 * | 8/2005 | Douglas | ................ | A61M 5/158 604/167.05 |
| 2005/0107743 A1 * | 5/2005 | Fangrow | ............... | A61M 5/158 604/164.01 |
| 2007/0213673 A1 * | 9/2007 | Douglas | ................ | A61M 5/158 604/167.05 |
| 2008/0243085 A1 * | 10/2008 | DeStefano | ........ | A61M 5/14248 604/180 |
| 2011/0082438 A1 * | 4/2011 | Beck | ..................... | A61M 5/142 604/500 |
| 2012/0029483 A1 * | 2/2012 | Griffith | ............... | A61J 15/0015 604/535 |
| 2014/0031754 A1 * | 1/2014 | Williams | ......... | A61M 39/10114 604/175 |

FOREIGN PATENT DOCUMENTS

EP         2 298 406 A1    3/2011
WO    WO 2012/117648 A1    9/2012

* cited by examiner

*Primary Examiner* — Kevin C Sirmons
*Assistant Examiner* — William Carpenter
(74) *Attorney, Agent, or Firm* — Dority & Manning, P.A.

(57) ABSTRACT

A connector for coupling to a base of medical device equipped with a circular hub having an annular recess. The connector includes a cap having a top surface, a bottom surface, a circumferential region defining a bottom plane and a periphery, and at least two arms substantially parallel to the bottom plane. Each arm spans at least two portions within the circumferential region to releasably engage the annular recess. At least one deflection member that is accessible from the top surface is positioned to deflect the arms. Pressing the connector onto the circular hub engages the arms with the annular recess so the connector can rotate completely about the circular hub. Pressing at least one deflection member to reversibly deflect at least one arm between its two portions of the circumferential region towards the periphery disengages the arm from the annular recess to decouple the connector.

14 Claims, 11 Drawing Sheets

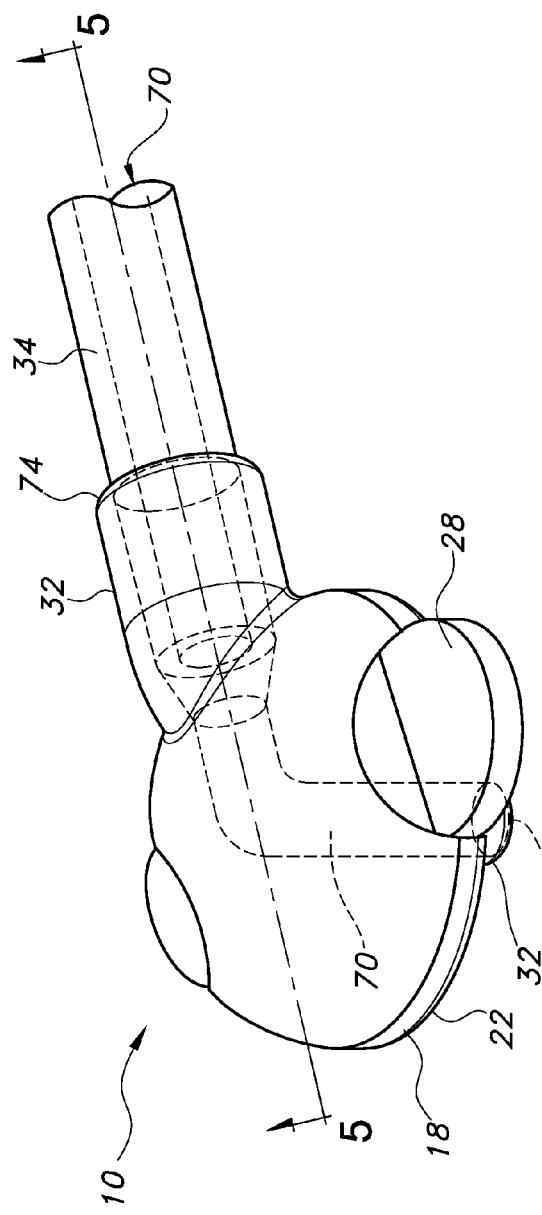
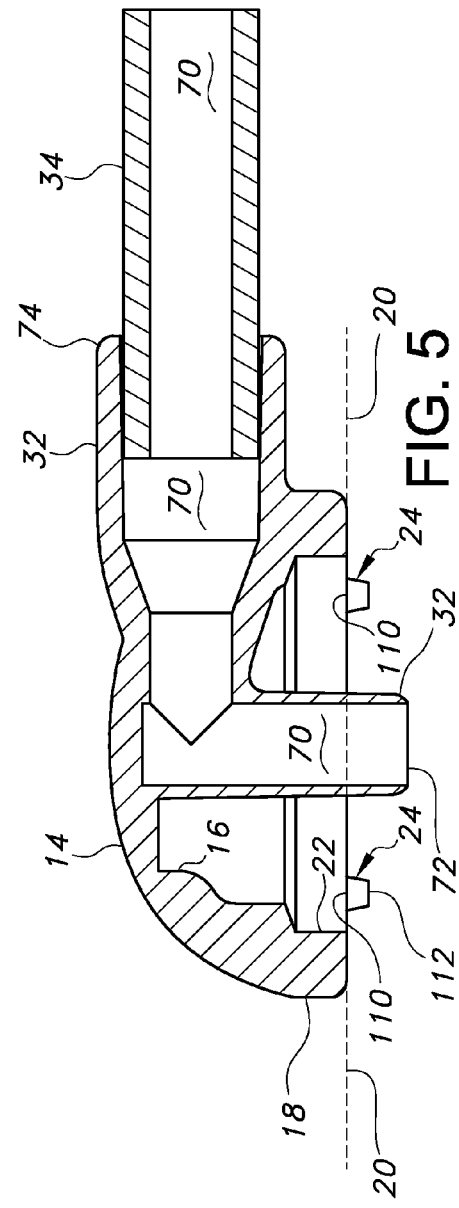
FIG. 4
FIG. 5

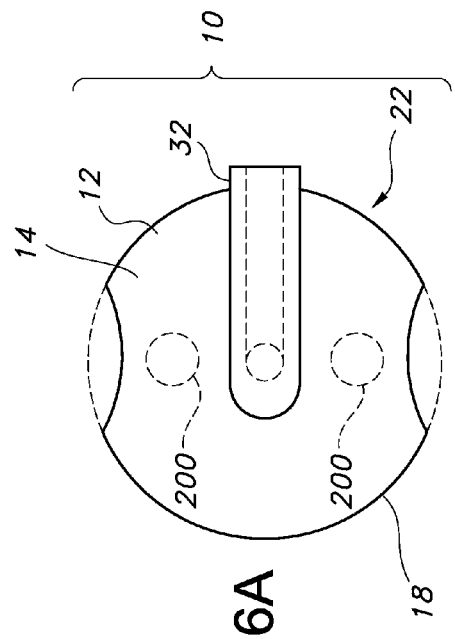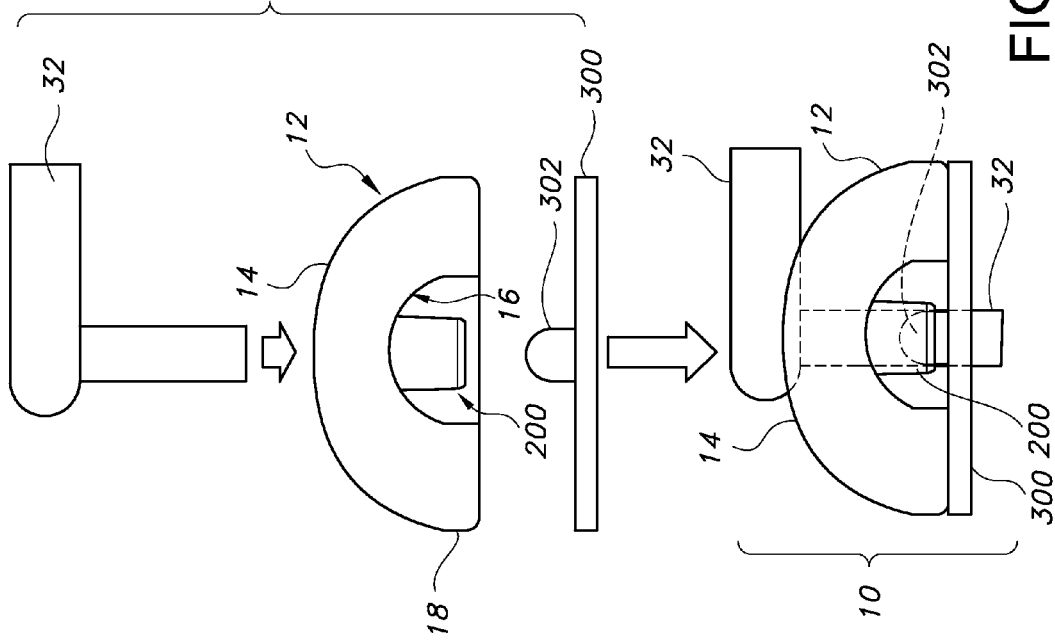

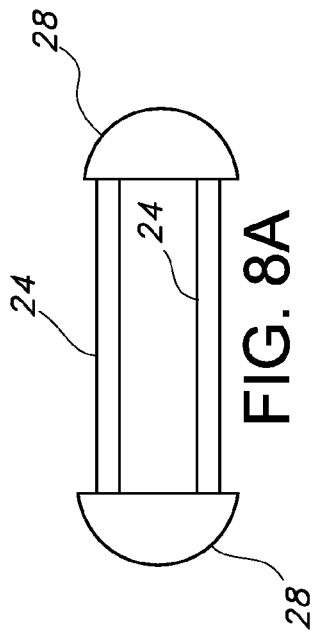
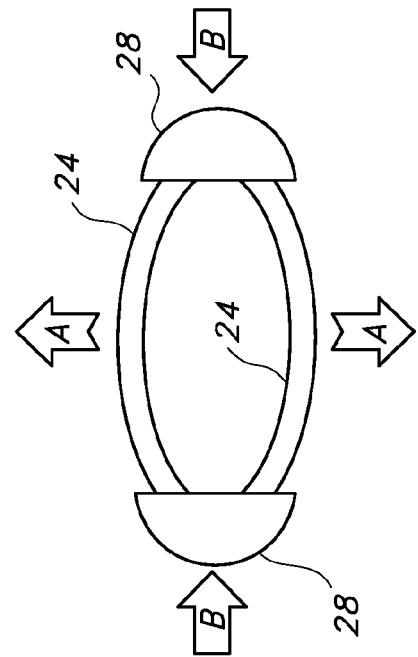
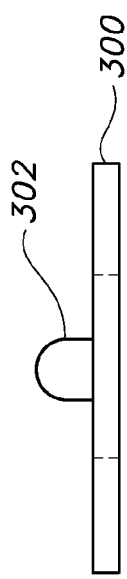
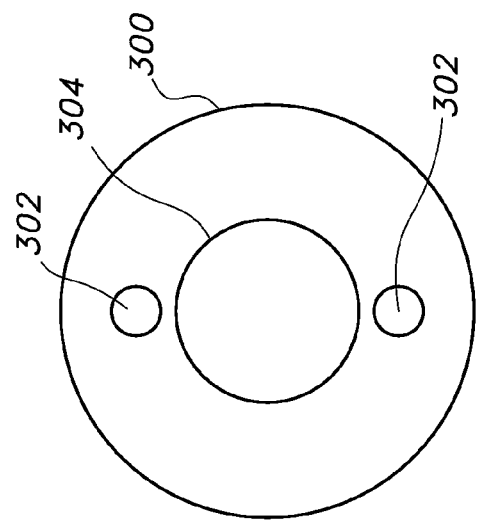

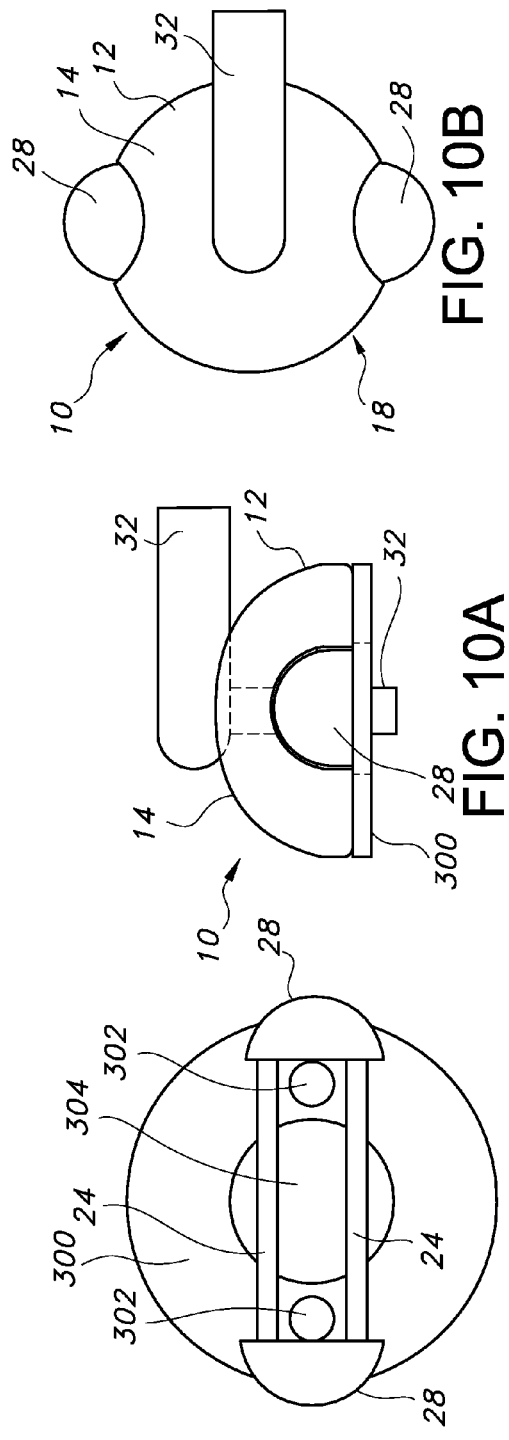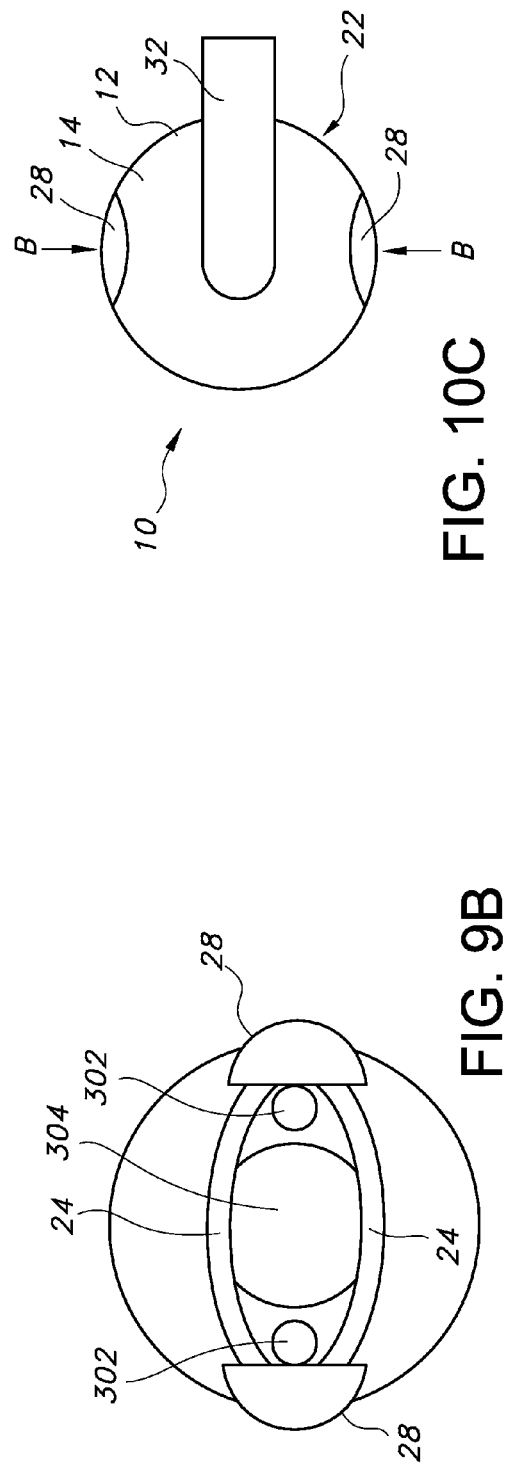

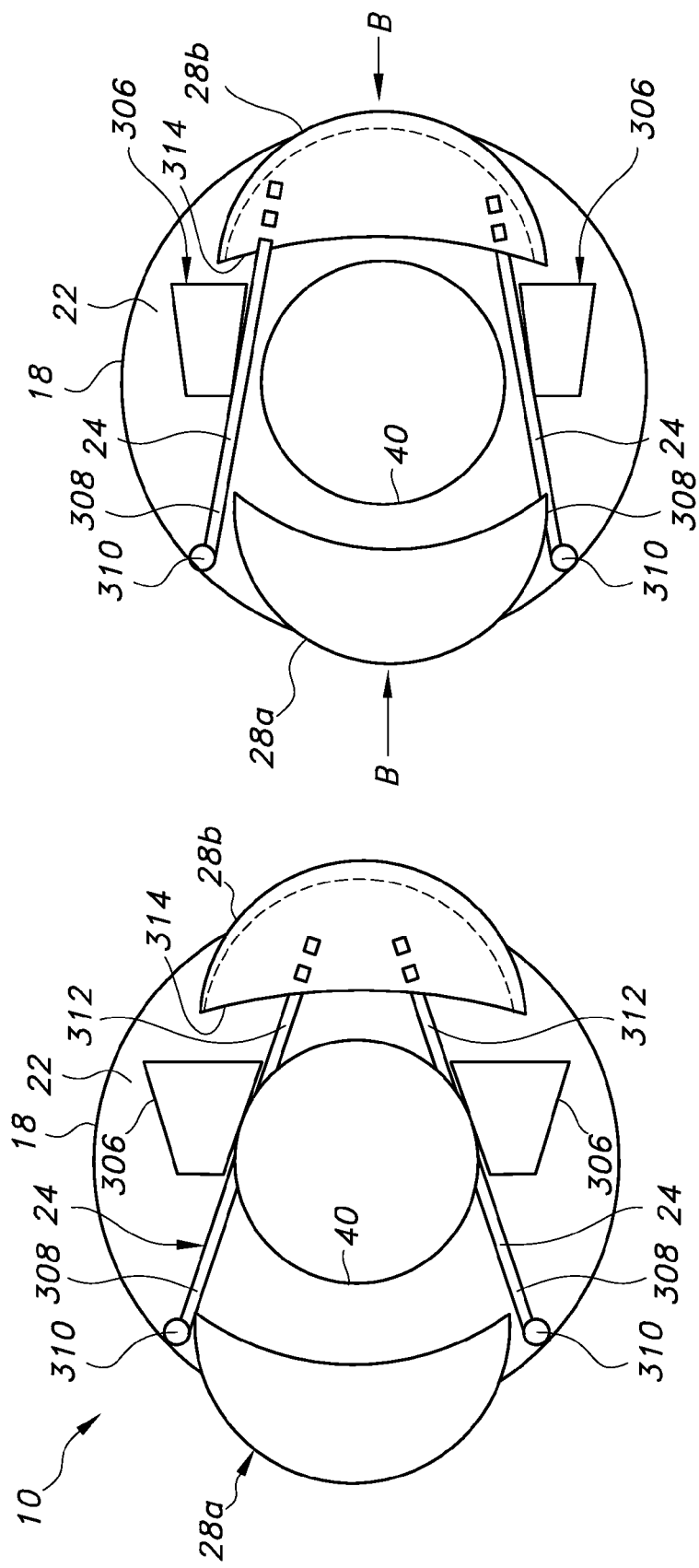

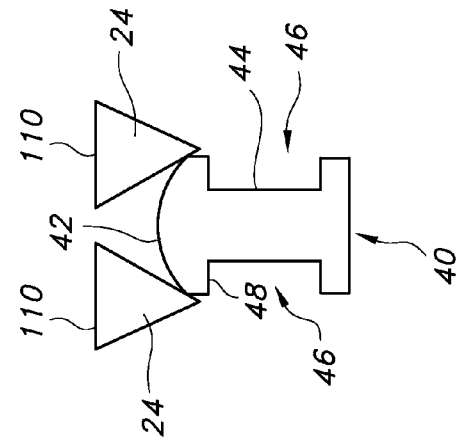
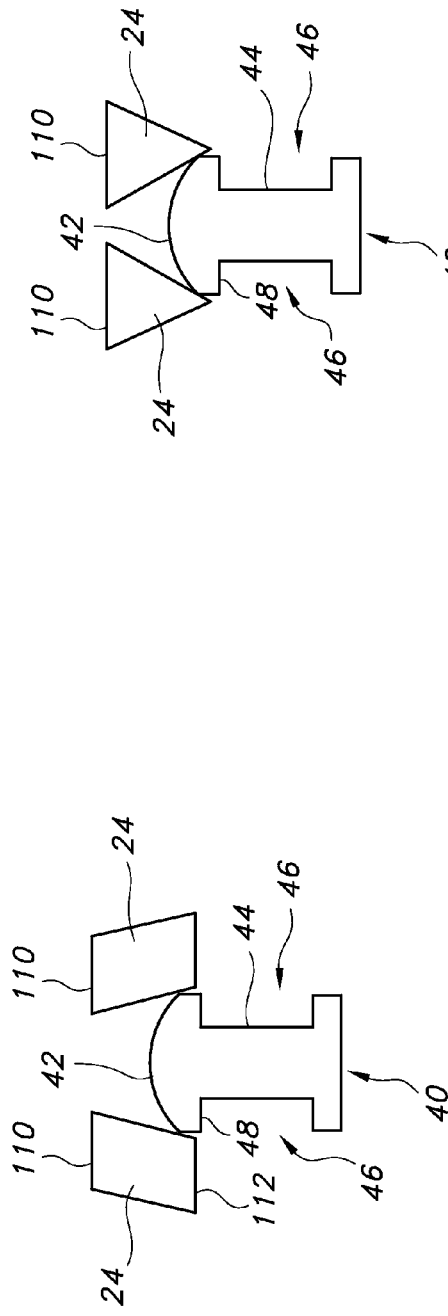
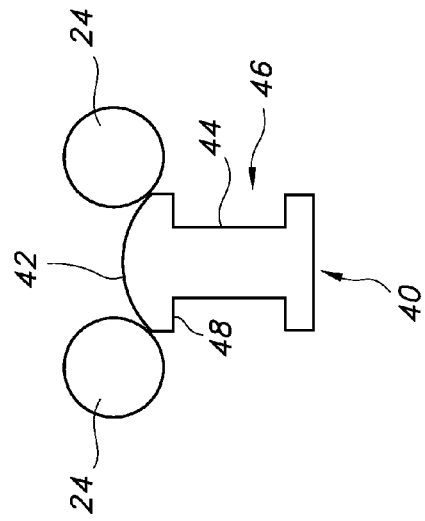
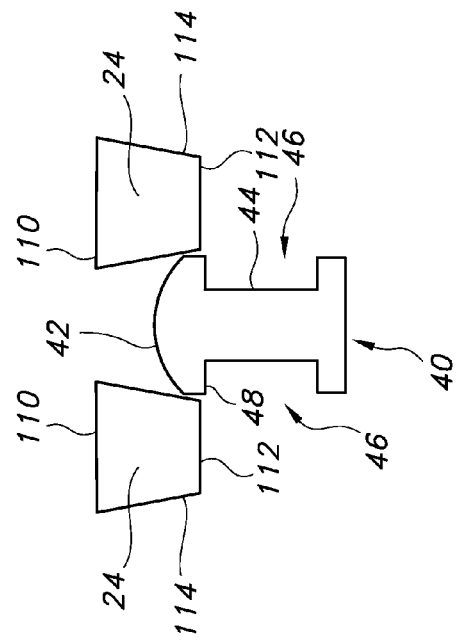

MEDICAL CONNECTOR WITH SPANNING ARMS

FIELD OF THE INVENTION

The present invention relates to improved connectors that convey fluids from a supply tube to an indwelling catheter. More particularly, it relates to an extension set with a particular connector which joins to an enteral feeding device.

BACKGROUND

Numerous situations exist in which a body cavity needs to be catheterized to achieve a desired medical goal. One relatively common situation is to provide nutritional solutions or medicines directly into the stomach or intestines. A stoma is formed in the stomach or intestinal wall and a catheter is placed through the stoma. This surgical opening and/or the procedure to create the opening is common referred to as "gastrostomy". Feeding solutions can be injected through the catheter to provide nutrients directly to the stomach or intestines (known as enteral feeding). A variety of enteral feeding devices have been developed over the years, including some having a "low profile" exterior portion which sits on a patient's skin, as well as those having the more traditional or non-low profile configurations. These enteral feeding devices are also known as "percutaneous transconduit catheters", "percutaneous transconduit tubes", "gastrostomy catheters", "percutaneous gastrostomy catheters", "PEG catheters" or "enteral feeding catheters". U.S. Pat. No. 6,019,746 for a "Low Profile Balloon Feeding Device" issued to Picha et al. on Feb. 1, 2000, provides an example of one device.

An enteral feeding device serves as the pathway through the stoma for transconduit of feeding solution into the stomach or intestine. During feeding, the enteral feeding device is often linked to the feeding solution via a tube with a connector. When combined the tube and connector form an extension set. Because a pressurizing source, e.g. a pump that drives the feeding solution through the tube and into and through the enteral feeding device, and because feeding may take several hours, e.g. overnight while a patient is sleeping, maintaining a robust and leak proof connection between the tube and the enteral feeding device is an important feature of the connector. It is also very desirable that the connection withstand twisting, torquing and pulling forces generated by movement of a patient.

However, a problem of low profile and non-low profile enteral feeding devices is the difficulty in connecting and disconnecting the extension sets to and from the enteral feeding device base or head. Many prior art enteral feeding devices have a low profile base and an indwelling catheter which extends from the base. A distal end of the catheter of such a device/assembly often includes a balloon which may be expanded to hold the catheter in a position in a body lumen, such as a stomach lumen.

An enteral feeding device often uses a plug to occlude the feeding passage opening in the base. This plug is attached to the device by a tether. Prior to connecting an extension set to such a conventional enteral feeding device, the step of removing the plug from the base to allow access to the feeding passage opening is required.

Other conventional enteral feeding devices are designed with a base or "head" having a locking cover member in the feeding passage opening to an indwelling catheter. The locking cover member is configured to receive a mating or interlocking connector. Generally speaking, these locking cover members have a keyway, a groove, and a stop member and they incorporate a slot to provide a design that is similar to the female portion of a bayonet fitting. A suitable connector that fits into the locking cover member has a dispensing projection and a key portion attached to that projection. Such a connector is pushed into the locking cover member and twisted in place until it interlocks. Exemplary illustrations of these conventional features may be found in the above referenced U.S. Pat. No. 6,019,746.

Connecting, changing and/or disconnecting a tube having an interlocking connector to/from a locking cover member like that of U.S. Pat. No. 6,019,746 can be a surprisingly difficult. When visibility of the base of the enteral feeding device is limited, e.g. if the patient is overweight, if it is dark, aligning and maneuvering the interlocking connector in or out of the base must rely on touch only. If the patient has impaired motor skills, fitting an interlocking connector in the locking cover member presents challenges of positioning, pushing and twisting. Yet, without being sure that this type of connector is correctly connected to the device, there is a risk of leaking gastric contents and or feeding solution onto a patient's skin surface, clothing, and the like. Further, when this type of connector sits tightly within the base, it may be difficult to remove, thereby requiring extensive pulling, movement of the connected extensions set and base and even unwanted displacement of the base, all of which can cause leakage or irritate a sensitive stoma site.

Some conventional interlocking connectors are configured to allow partial rotation within the base after the connector has been fitted in place. That is, after the inserted interlocking connector in the locking cover member is twisted so the key portion travels past a "detent", the interlocking connector can rotate between a position where the key portion contacts a stop and a position where the key portion contacts a detent. Unfortunately, the limited range of motion allows the interlocking connector to transmit torquing force to the enteral feeding catheter. This transfer of force may cause the catheter to twist or pull which can cause leakage or irritate a sensitive stoma site. If sufficient force is inadvertently encountered, the key portion of the interlocking connector may be forced past the detent as it would be when a patient or care give is disconnecting the locking connector. After the key portion is forced past the detent, it can readily align with the slot/keyway thereby allowing the extension set to inadvertently become completely disconnected.

These conventional connectors have evident drawbacks that remain unresolved.

The popularity of enteral feeding devices having low profile heads or bases has also resulted in a conversion kit that provides a low-profile base or head component that is clamped onto a percutaneously inserted catheter (i.e., catheter tubing) that is inserted through the abdominal wall to a patient's stomach. Such a low-profile conversion kit is described in U.S. Pat. No. 5,549,657. According to that patent, base or head component has an anti-reflux valve assembly and a two-part clamp. After the base or head component is clamped on the end of a catheter, it functions as the base or head for the catheter. The anti-reflux valve assembly includes a circular seat. A recess located beneath the seat is configured to receive opposed lips of a snap-fit connector that snaps onto the circular seat. An example of such a low-profile conversion kit is commercially available as the Gaurderer Genie™ PEG System Kit available from Bard Nordic (Helsingborg, Sweden), a subsidiary of C.R. Bard Inc.

When a patient is ready to be fed using such a snap-fit connector, the connector is snap fitted onto the anti-reflux valve assembly by pressing the connector against the anti-reflux valve assembly to urge the lips of the connector over the circular seat and into the recess located beneath the circular seat. When feeding is complete, the snap-fit connector is removed by prying or pulling on a set of opposed, reinforced ears. Attachment and detachment of the snap-fit connector is facilitated by a set of opposed slots that enhances axial and radial distortion and flexure of only the central portion of the snap-fit connector when a force is applied to one or both of the opposed ears.

Connecting, changing and/or disconnecting a snap-fit connector to/from such a low-profile enteral feeding head or base may also be a surprisingly difficult exercise at least for the same reasons as conventional interlocking connector. Moreover, the application of force to press the snap-fit connector onto the head and also to pry it off the head transfers forces directly to the enteral feeding device which may create discomfort and cause irritation to the sensitive stoma site. The low-profile of the head and its relatively small size (e.g., typically between about 13 mm and 25 mm in diameter) also creates difficulty in that opposed ears of the snap-fit connector can extend over the ends of the head and lie adjacent or even against the skin of the patient to make it difficult to grasp or pinch the ears between the fingers.

Accordingly, there is a need for a connector for coupling a medical fluid supply tube to the head of a catheter device having a circular hub. For example, there is a need for an enteral feeding extension set connector which permits a user or health care provider to easily connect and disconnect an extension set to the base of an enteral feeding device. Such a system would permit a user or health care provider to easily and reliably disconnect the previous, used, connector and connect a new connector, desirably without needing to see the base of the device.

SUMMARY

In response to the difficulties and problems discussed herein, the present invention provides a connector for coupling a medical fluid supply tube (e.g., "the tube") to a base of a catheter device (e.g., an enteral feeding device) when the base is equipped with a circular hub having a radius, a top surface, a side surface, and an annular recess defined in the side surface. The invention is exemplified with respect to connection to enteral feeding devices and delivery of feeding solutions, but other devices with circular hubs and other fluids (liquids and/or gases) are envisioned.

The connector is composed of a cap having a top surface, a bottom surface, and a circumferential region defining a bottom plane and a periphery. The cap further includes at least two arms substantially parallel to the bottom plane. Each arm spans at least two portions within the circumferential region to releasably engage the annular recess. At least one deflection member that is accessible from the top surface is configured to deflect the arms. The connector couples to the circular hub by positioning the connector on the circular hub and pressing the connector downward (i.e., toward the catheter device) to engage the arms with the annular recess. To decouple the connector, at least one deflection member is pressed so as to reversibly deflect at least one arm between its two portions of the circumferential region towards the periphery and disengage at least one arm from the annular recess.

In an aspect of the invention, each arm may have a top surface configured to releasably engage the annular recess defined in the side surface of the circular hub and a bottom surface of the arm may be beveled. The connector is rotatably coupled to the circular hub on the base of the catheter device. That is, when coupled to the base of the catheter device, the connector may rotate completely about the circular hub in either direction of rotation without inadvertently decoupling from the catheter device or causing the catheter device to twist. Desirably, the connector will provide relatively little resistance to rotation so it may move readily in response to twisting or other forces to avoid kinking the feeding tube or transferring force to the catheter device.

A conduit may define a fluid pathway through the connector and can be configured to direct a feeding solution to a lumen of the catheter device. The fluid pathway may be spatially positioned or located to pass between the arms. The fluid pathway may bend such that the fluid pathway has one section that has an orientation different from the lumen of the catheter device, such as a 90 degree bend so that a pathway section is generally perpendicular to the lumen of the catheter device. Alternatively, the fluid pathway may be configured to have the same orientation as the lumen of the catheter device. Such a configuration is desirable for delivering a bolus of feeding solution. The conduit at the proximal end of the connector may be in the form of a nozzle that is configured to engage an orifice or passageway opening defined in the hub to supply a feeding solution through the indwelling catheter of a catheter device. Alternatively, the conduit may be configured to engage a nozzle protruding from the surface of the hub to supply a feeding solution to the indwelling catheter of a catheter device.

The connector may further include motion limiters to limit the pitch of the connector. These motion limiters may be configured to contact an upper surface of the hub or an upper surface of the base of the catheter device.

In an aspect of the invention, the cap, the arms, and the deflection member(s) may be formed from different materials. Alternatively, the cap, the arms, and/or the deflection member(s) may be unitary or monolithic and may be formed of the same material. In another aspect of the invention, the cap may have a port located above each arm where it engages the annular recess of the cap to permit visual inspection of engagement between the arm and the annular recess defined in the side surface of the circular hub. In another aspect of the invention, each arm may be reversibly displaced when a force of between about 2 Newtons and about 14 Newtons is applied to its respective deflection member.

The present invention also encompasses an enteral feeding assembly. The enteral feeding assembly is composed of: (i) an enteral feeding device having a base and including at least one indwelling catheter or tube with a lumen positioned through the base, the base having at least one circular hub having a radius, a top surface, a side surface and an annular recess defined in the side surface; and (ii) an extension set with a connector as generally described above for rotatably coupling the extension set to the base of the enteral feeding device wherein the connector allows for fluid communication between the extension set and the lumen of the enteral feeding device.

The present invention further encompasses an extension set. The extension set includes a medical fluid supply tube and a connector in fluid communication with the tube, the connector configured for use with an enteral feeding device having a circular hub is a connector as generally described above.

BRIEF DESCRIPTION OF THE DRAWINGS

FIG. 4 is a perspective view illustrating a detail an exemplary connector including a conduit.

FIG. 5 is a cross-sectional view illustrating a detail an exemplary connector including a conduit from FIG. 5, taken along line 5-5.

FIG. 6A is an exploded side view illustrating details of selected components of an exemplary connector. This figure excludes certain components such as arms and deflection members for ease of illustration.

FIG. 6B is a side view illustrating details of selected components of an exemplary connector. This figure excludes certain components such as arms and deflection members for ease of illustration.

FIG. 6C is a top view illustrating details of selected components of an exemplary connector. This figure excludes certain components such as arms and deflection members for ease of illustration.

FIG. 7A is a side view illustration of an optional bottom plate from an exemplary connector, the illustration showing details of certain components.

FIG. 7B is a top view illustrating details of an optional bottom plate from an exemplary connector, the illustration showing details of certain components.

FIG. 8A is a top view illustrating details from an exemplary connector, the illustration showing the arms and the deflection members in an unstressed or un-deflected state.

FIG. 8B is a top view illustrating details from an exemplary connector, the illustration showing the arms deflected towards the periphery in the direction of arrows "A" when the deflection members are pressed inwards in the direction of arrows "B" by a force to render the arms in a stressed or deflected state.

FIG. 9A is a top view illustrating details from an exemplary connector, the illustration showing exemplary arms and deflection members positioned on a bottom plate with the arms bracketing male connection elements on the bottom plate. The illustration shows the arms and the deflection members in an unstressed or un-deflected state.

FIG. 9B is a top view illustrating details from an exemplary connector, the illustration showing exemplary arms and deflection members positioned on a bottom plate with the arms bracketing male connection elements on the bottom plate. The illustration shows the arms and the deflection members in a stressed or deflected state with the male connection elements limiting the inward travel of the deflection members.

FIG. 10A is a side view of an exemplary connector.

FIG. 10B is a top view of an exemplary connector of FIG. 10A, the illustration shows the deflection members (with the arms not shown) in an unstressed or un-deflected state.

FIG. 10C is a top view of an exemplary connector of FIG. 10A, the illustration shows the deflection members (with the arms not shown) in a stressed or deflected state.

FIG. 11A is a bottom view of an exemplary connector and a section of a circular hub of a catheter device with the connector engaged with the annular recess of the circular hub. The illustration shows the deflection members and the arms in an unstressed or un-deflected state.

FIG. 11B is a bottom view of an exemplary connector and a section of a circular hub of a catheter device with the connector disengaged with the annular recess of the circular hub. The illustration shows the deflection members and the arms in a stressed or deflected state.

FIGS. 14A to 14D are side cross-section view illustrations showing various exemplary arms located above the recess of the circular hub.

DETAILED DESCRIPTION

Figure 1:
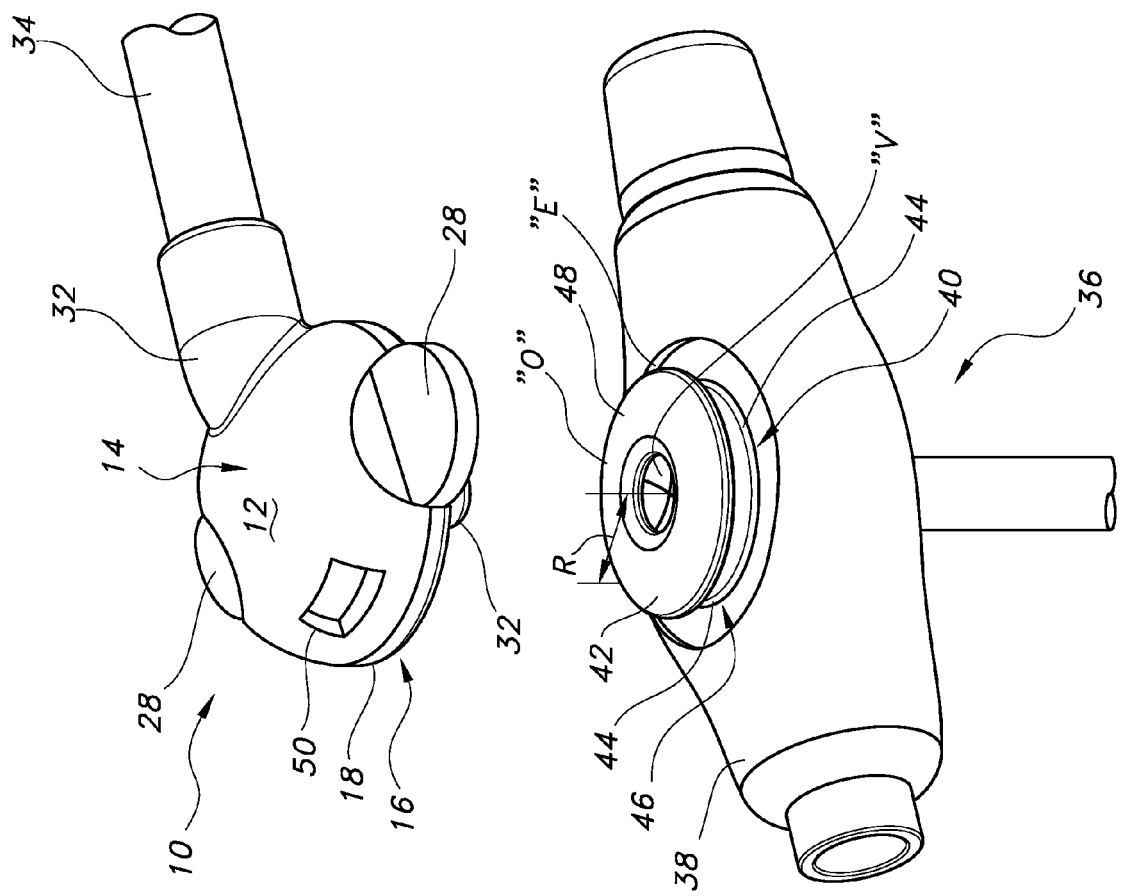
FIG. 1 is a perspective view illustrating an exemplary connector for coupling an extension set to an enteral feeding device having a circular hub.

Reference will now be made in detail to one or more embodiments, examples of which are illustrated in the drawings. It should be understood that features illustrated or described as part of one embodiment may be used with another embodiment to yield still a further embodiment. It is intended that the claims include these and other modifications and variations as coming within the scope and spirit of the disclosure.

Turning now to the drawings, FIG. 1 of the drawings is a perspective view illustrating an exemplary connector for coupling a medical fluid supply tube (i.e., the tube) to a base of a catheter device (e.g., an enteral feeding device) having a circular hub. As used herein, the term "fluid" encompasses liquids, gases and combinations thereof. Liquids include nutritional liquids and feeding solutions that may be supplied to a patient through the tube. An example of a gas may be a gas vented from the stomach or intestine of a patient. The connector 10 (which may sometimes be referred to as an "extension set connector" or "feed tube connector" or "tube connector") has a cap 12. The connector cap 12 has a top surface 14, a bottom surface 16, and a circumferential region 18 defining a bottom plane 20 (not shown in FIG. 1) and a periphery 22 (not shown in FIG. 1). The cap 12 includes at least two arms 24 (not shown in FIG. 1) substantially parallel to the bottom plane 20. Each arm 24 spans at least two portions 26 within the circumferential region 18. The cap 12 further includes at least one deflection member 28 in communication with the arms 24 to deflect the arms. The deflection member(s) 28 is/are desirably accessible from the top surface 14 of the cap 12.

In an aspect of the invention, one or more of the arms 24 can be resilient. The arms 24 may be resilient over all or substantially all, or the arm 24 may be resilient in one region and non-resilient in another region. For example, the arm 24 may be resilient within the circumferential region 18 and less resilient or not resilient away from the circumferential region 18. As used herein, the term "resilient" refers to the ability of a material to be able to recoil or spring back into shape after bending, stretching, or being compressed. With respect to the present invention, the arms 24 or a portion thereof may be made of a resilient material that can be reversibly displaced. Suitable materials include polyethylene terephthalates, polypropylenes, high and low density polyethylenes, nylons, polyurethanes, silicones, and natural and synthetic elastomers. Blends and combinations of these materials may be used. These materials desirably form an arm that can be readily displaced and which will revert to its original shape or condition. Alternatively, the arm may be substantially rigid but displaceable or deflectable and the deflection member may be resilient such that the arms 24 can be reversibly displaced.

The connector may also include a conduit 32 defining a fluid pathway for transferring feeding solution from the tube 34 to the lumen of an enteral feeding device 36.

The extension set connector 10 is shown in FIG. 1 positioned above an enteral feeding device 36 that is equipped with a base 38 having a circular hub 40. The circular hub has a radius "R", a top surface 42, a side surface 44, and an annular recess 46 defined in the side surface 44. In other words, the circular hub 40 has a generally horizontal top surface 42 that extends over a generally vertical side surface 44 forming rim, collar, rib, lip or flange structure 48 that defines an underlying annular recess 46 which is sized to engage the arms 24 of the connector 10. The radius "R" is the distance from the center of the hub 40 to the outermost edge "E" of the portion of the top surface 42 forming the rim, collar, rib, lip or flange structure that 48 defines the recess 46. The circular hub 40 also includes a passageway opening or orifice "O" at the center of the hub. A valve "V" is desirably used to seal the orifice "O" when the connector 10 is not engaged with the circular hub 40.

Figure 13:
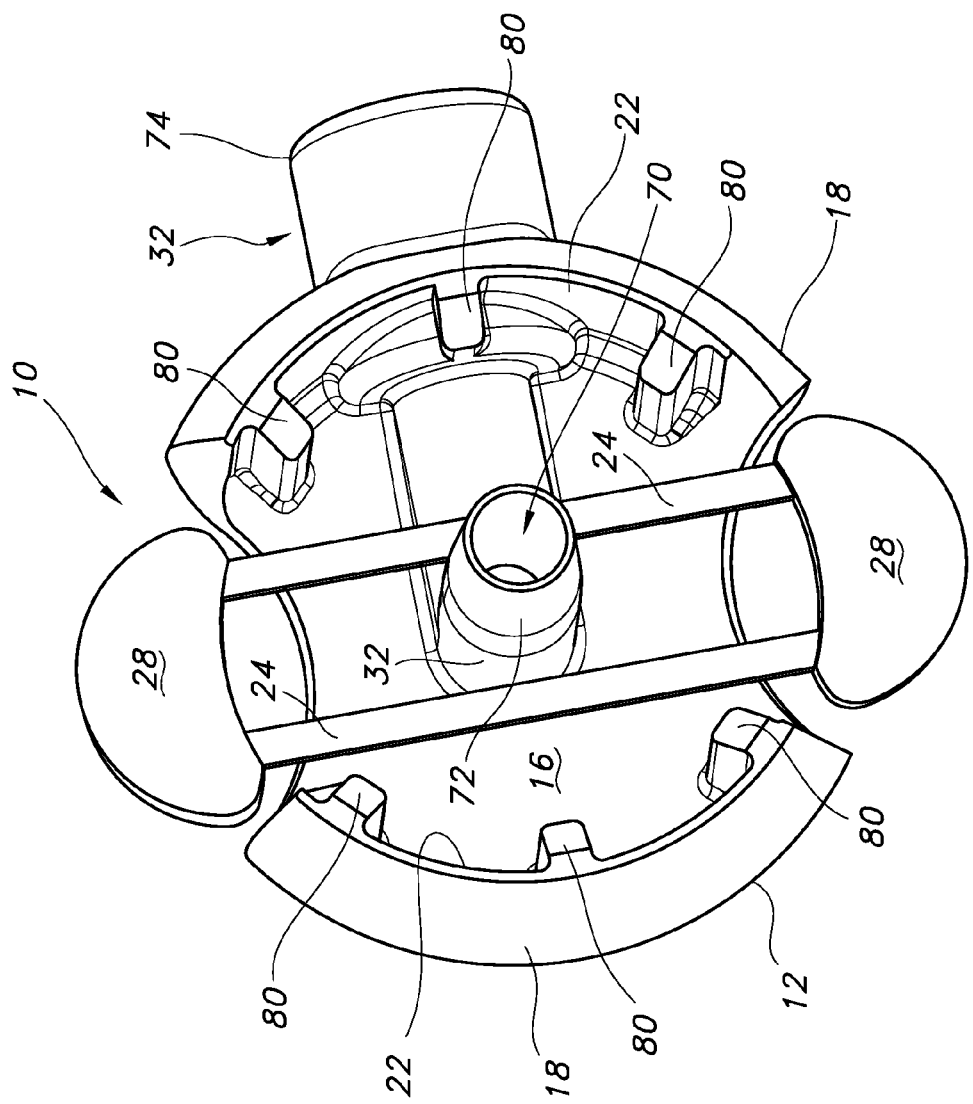
FIG. 13 is a bottom view of an exemplary connector.

Generally speaking, the arms 24 are configured to releasably engage the annular recess 46 defined in the side surface 44 of the circular hub 40. The arms 24 are shown in FIG. 13 which is a bottom view of an exemplary connector. Examples of other arms 24 may also be seen in FIGS. 8A, 8B, 9A, 9B, 11A and 11B. The connector 10 is coupled to the circular hub 40 by pressing the connector downwards onto the hub until the arms engage the annular recess defined in the side surface of the circular hub. Of course, the connector 10 may be coupled to the circular hub 40 by squeezing deflection members 28 between the fingers so the arms are deformed or displaced such that they clear the outermost edge "E" of the top surface 42 forming the rim, collar, rib, lip or flange structure 48, seating the connector 10 on the circular hub 40 and then releasing the squeezing force on the deflection members 28 so the arms 24 engage the annular recess 46. The connector decouples from the hub by squeezing the deflection members 28 to reversibly displace the arms 24 towards the periphery 22 (e.g., radially outward from the hub 40) to disengage them from the annular recess 46. Desirably, the connector is rotatably coupled to the circular hub on the base of the enteral feeding device. That is, the connector may rotate completely about the circular hub in either direction of rotation without disconnecting from the enteral feeding device or causing the enteral feeding device to twist. It is desirable for the connector to be rotatably coupled such that it can rotate freely around the circular hub with relatively little resistance. Also shown in FIGS. 1, 2 and 3 is a port or opening 50 in the cap 12 that is above the location where each arm 24 engages the annular recess 46 to permit visual inspection of engagement between the arm 24 and the annular recess 46.

Figure 2:
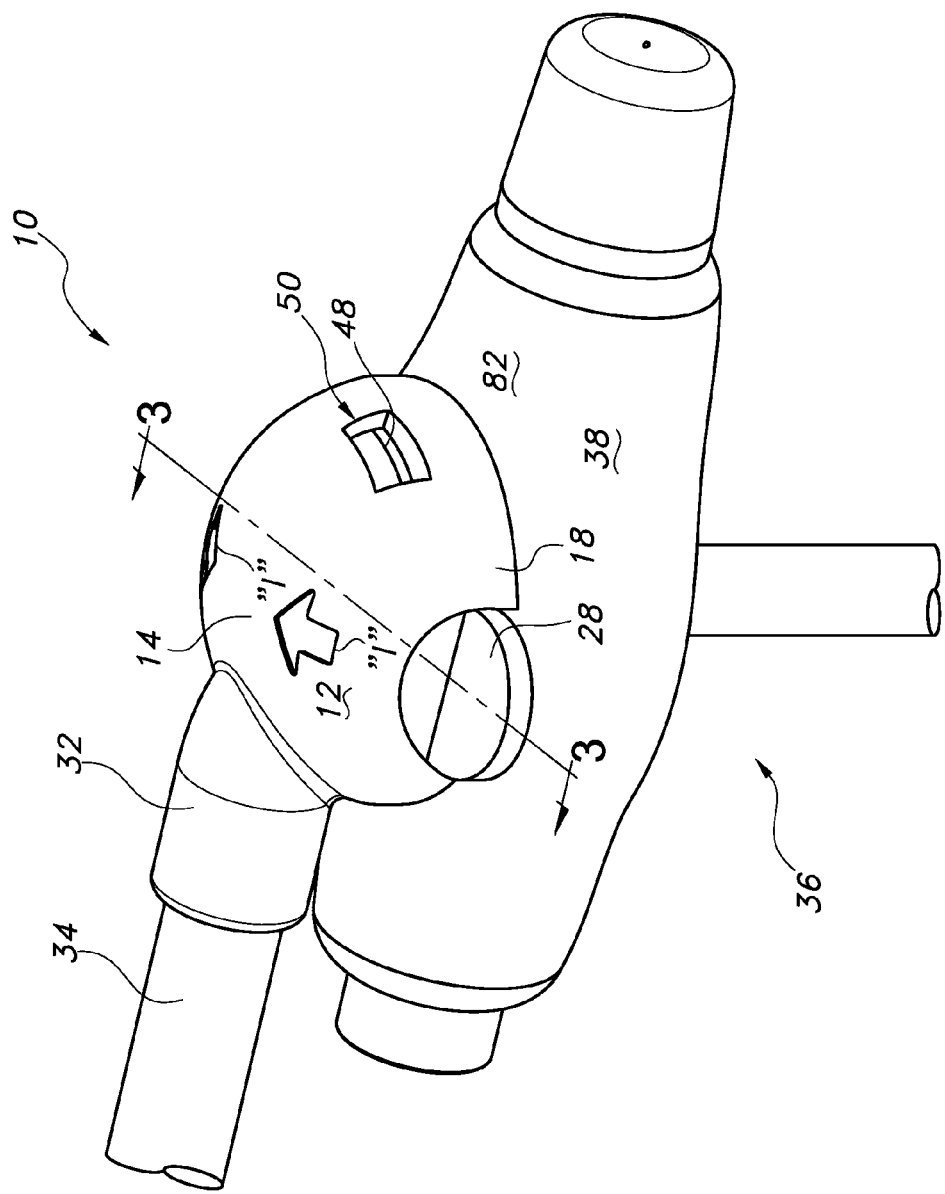
FIG. 2 is perspective view illustrating an exemplary connector of FIG. 1 coupled to an enteral feeding device having a circular hub.

Referring now to FIG. 2 of the drawings, there is shown in perspective view an illustration of the connector 10 coupled with the enteral feeding device 36. Illustrated in this view is the optional port 50 that allows visual inspection of the inspection of engagement between the arm 24 and the annular recess 46. More particularly, the outermost edge of the rim, collar, rib, lip, or flange structure 48 is visible through the port 50.

Figure 3:
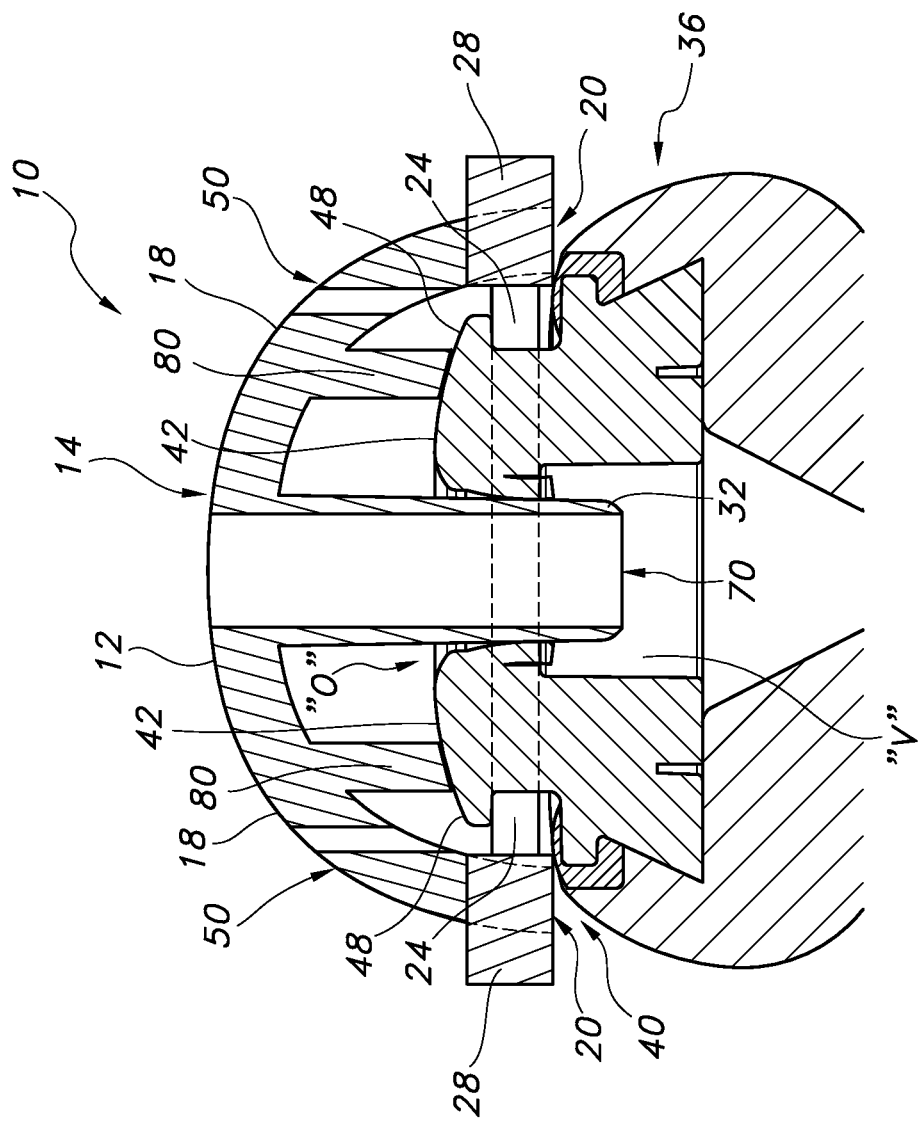
FIG. 3 is a side cross-sectional view illustrating a detail of a portion of an exemplary connector and a circular hub on a base of an enteral feeding device from FIG. 2, taken along line 3-3.

Referring now to FIG. 3 of the drawings, there is shown in side, cross-sectional view, an illustration showing details of the connector 10 from FIG. 2, taken along line 3-3, when coupled with the enteral feeding device 36. In this view, the cap 12 contacts the circular hub 40. A defined fluid pathway 70 may pass through conduit 32 of the connector 10. As indicated in FIG. 3, the arm 24 is engaged with the annular recess 46 defined in the side surface 44 of the circular hub 40. The arm is held in communication with the cap 12 by structure that is not illustrated in this FIG. 3. In addition, the connector 10 may further include motion limiters 80 to limit the pitch and/or roll of the connector (i.e., movements or oscillations about an axis that is parallel to the passageway opening defined in the hub and perpendicular to the upper surface of the hub or the upper surface of the base such that circumferential portions of the connector may move up or down and the opposed circumferential portions of the connector may move oppositely). More particularly, the cross-sectional view of FIG. 3 illustrates a pair of motion limiters 80 integrated with or joined to part of the cap 12 and configured to contact an upper surface of the hub 24. It is contemplated that the cap 12 and motion limiters 80 may be configured so the motion limiters 80 may contact an upper surface 82 of the base 38 of the enteral feeding device 36. Alternatively and/or additionally, the motion limiters 80 may constitute a portion of the conduit 32 or, more desirably, may constitute a portion of the arms 24 or deflection member 28.

Figure 12:
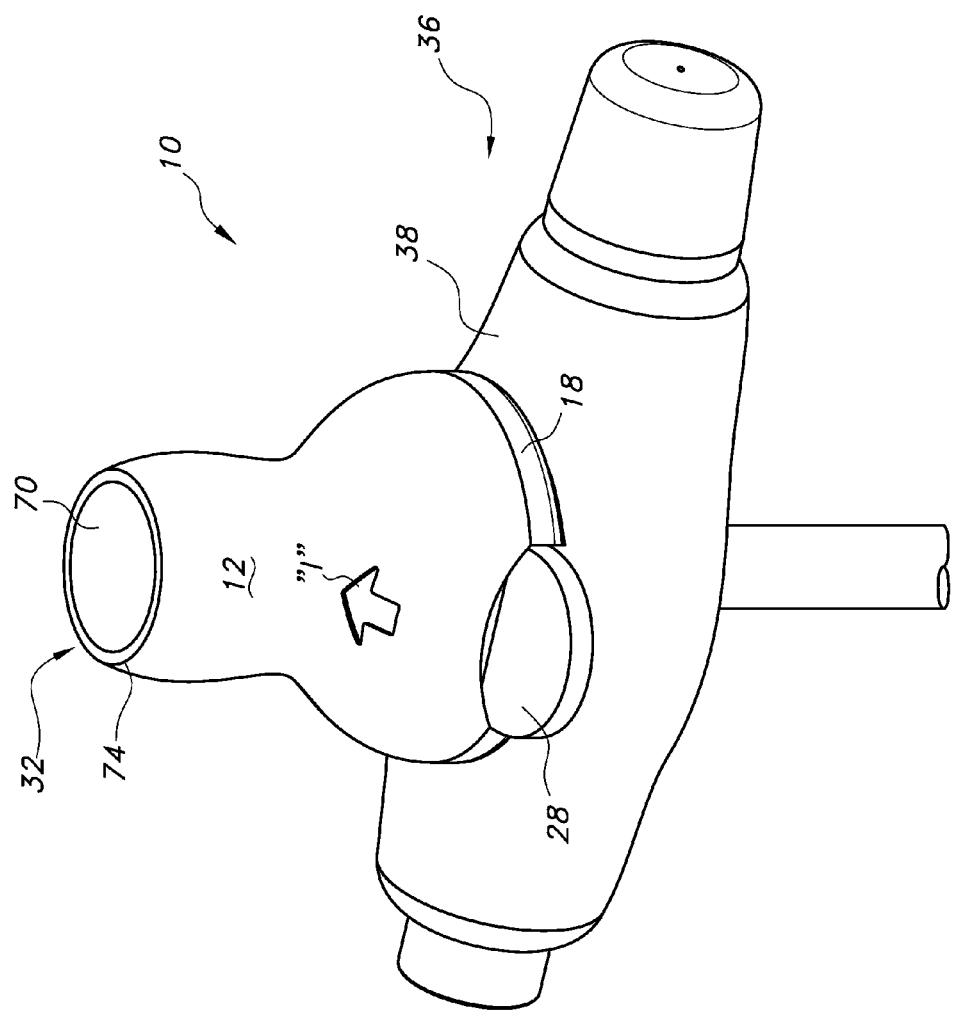
FIG. 12 is a side perspective view illustrating an exemplary connector in which both a proximal end and a distal end of a conduit defining a fluid pathway are axially aligned with the lumen of feeding catheter device and engaged with the base of the device.

The deflection member 28 may have topography to help the users identify the deflection member 28 through visual and/or tactile indicia such as, for example, bands, bumps, ridges, raised dots, random rough texture, contrasting color or the like. Alternatively and/or additionally, the cap 12 of the extension set connector 10 may include indicia "I" as illustrated in FIGS. 2 and 12. These indicia "I" may be used to provide a tactile or visual cue to a user about the location of the deflection members and/or the direction to press squeeze or pinch them.

Referring now to FIGS. 4 and 5, FIG. 4 shows a perspective view of a connector 10 including a conduit 32 defining a fluid pathway 70 through the connector and FIG. 5 shows a cross-sectional view of the connector 10 from FIG. 4, taken along line 5-5, including a conduit 32 defining a fluid pathway 70 through the connector. The conduit 32 is configured to supply a feeding solution from a tube 34 to a lumen of the enteral feeding device 36. A proximal end 72 of the conduit 32 defining the fluid pathway may be axially aligned with the lumen of the enteral feeding device and then may have a 90 degree bend such that a distal end 74 of the conduit 32 extends in a generally perpendicular manner to proximal end 72. This configuration is useful for most feeding applications. Alternatively, the proximal end 72 of the conduit 32 defining the fluid pathway 70 may be axially aligned with the lumen of the enteral feeding device and then may continue such that the distal end 74 of the conduit 70 continues to extend in an axially aligned manner to proximal end. Such a configuration is illustrated in side perspective view in FIG. 7, which shows the extension set connector 10 coupled with the base 38 of an enteral feeding device 36. Such a configuration is desirable for delivery of a bolus of feeding solution. The conduit 32 may form a nozzle as generally illustrated in FIGS. 3, 5, 6A, 6B, 10A, and 13 that is configured to extend beyond the bottom plane 20 of the connector to engage an orifice "O" defined in the hub 40 to supply a feeding solution to a lumen defined by the indwelling catheter of an enteral feeding device. Alternatively, the conduit 32 may be configured to engage a nozzle (not shown) protruding from the top surface of the hub to supply a feeding solution.

Generally speaking, the connector 10 is positioned directly over the circular hub 40 for coupling. As the connector is depressed onto the circular hub, the connector contacts these regions of the circular hub to couple the connector the circular hub 40: top surface 42, edge "E" and the rim or flange structure 48, and annular recess 46. The arms 24 of cap 12 readily deflect as downward force is applied to the connector and the arms 24 slide past the upper edge "E" of the rim or flange structure 48 on the circular hub 40 (as shown in FIG. 3). The top surface of the arms 110 engage the annular recess 46 defined in the side surface 44 of the circular hub 40. The arms 24 are configured to releasably engage an underside (not shown) of the generally horizontal top surface 42 that extends over the generally vertical side surface 44 forming rim, collar, rib, lip, or flange structure 48 that defines the annular recess 46.

The downward force needed to accomplish the coupling is generally less than about 10 Newtons and is desirably between about 0.1 Newtons and 8 Newtons. Such a low level of force is very important because the downward force is transferred directly to the enteral feeding device which resides in the sensitive stoma site. This configuration avoids the much higher levels of forces that are required to couple a snap-fit connector into place. Unlike such "high force" coupling connectors, the present invention avoids irritating the sensitive stoma site; the low level of force used to engage the connector helps patients that are mobility impaired, sight impaired, or who otherwise have difficulty seeing or reaching the feeding device (e.g., obese patients, patients with poor motor skills, etc.).

The arms 24 also provide a positive tactile signal when they catch the annular recess 46 defined in the side surface 44 of the hub. The arms 24 may transmit the feeling of increasing resistance as they progressively slide against top surface 42 and radially deflect towards and around the dimensions defined by edge "E" as the connector is pressed onto the hub. Such resistance immediately dissipates when the arms enter the recess to provide a tactile signal. This action may also produce an audible signal that may be characterized as a "snap" or "click" to alert the user that the catches are correctly positioned in the recess. These tactile and audible signals help communicate to users and care providers that a proper and secure connection is made.

According to the invention, the connector 10 decouples from the circular hub 40 by squeezing or pressing deflection member 28 to reversibly displace the arms 24 radially outward toward the periphery 22. When the deflection members 28 are pressed or squeezed, the arms 24 spatially move radially outward and away from the circular hub 40 so that they are at or clear the edge "E" of structure 48. The displacement of the arms 24 results from the flexing or deformation of the arms. For example, each arm 24 may be made of a material such that it takes on a changed, but reversible spatial configuration when its respective deformation member 28 is subjected to a force of between about 2 and about 14 Newtons. Exemplary materials include, polyethylene terephthalates, polypropylenes, high and low density polyethylenes, polyurethanes, nylons, natural and synthetic elastomers, and silicones that are not "brittle" and combinations/blends thereof. It is contemplated that the arms may have regions that are thinner than the other portions. Alternatively and/or additionally, it is contemplated that the arms may be pre-curved or bent to preferentially deform in a particular direction. It is also contemplated that the arms may have a graduated thickness or varying levels of thickness to enhance their resilient characteristics, or to control the extent and/or location of resiliency such that each is reversibly deformable. A feature of the present invention is that the arms are reversibly deformable to engage and disengage the hub. By manipulating the resilience of the arms (rather than requiring the entire cap to be resilient), it is thought that the force needed to engage and disengage the connector from the circular hub can be more carefully controlled to avoid transferring force to a patient, which may cause irritation (e.g., of a stoma site), and to allow secure connection/disconnection without requiring an undesirably high level of force.

Referring now to FIGS. 6A, 6B and 6C of the drawings, there is shown an illustration of selected components of an exemplary connector 10. FIG. 6A is an exploded side view illustration of these selected components of the connector 10 including a cap 12 having a top surface 14, a bottom surface 16 which includes female connection elements 200, a circumferential region 18, a conduit 32, and an optional bottom plate 300 which includes male connection elements 302. FIG. 6B illustrates how these components fit together into connector 10. Both FIGS. 6A and 6B exclude the arms and deflection member for ease of illustration. FIG. 6C is a top view illustration of the assembled components of FIG. 6B. This view also excludes the arms and deflection member for ease of illustration, but does illustrate the top surface 14, the top of the conduit 32, the periphery 22 of the circumferential region 18 (with female connections 200 in phantom).

FIG. 7A is a side view illustrating an optional bottom plate 300 of an exemplary connector 10 showing a male connection element 302 which couples with the female connection element 200 of the cap 12. FIG. 7B is a top view of the optional bottom plate 300 showing the male connection elements 302 and an aperture 304 through the plate 300. The aperture 304 allows insertion of the circular hub 40 of the enteral feeding device through the bottom plane 20 to an interior of the cap 12.

FIG. 8A is a top view of an exemplary configuration of a pair of arms 24 and the deflection members 28. In this illustration, the arms 24 are in an un-deflected configuration. As seen in the top view illustration of FIG. 8B, the pair of arms 24 are deflected towards the periphery 22 of the cap 12 (not shown in this illustration) in the direction shown by the arrows "A" when the deflection members 28 are pressed inwards by force "B" to arrive at the illustrated deformed or deflected state. The original state of the arms 24 in an un-deflected configuration and the deflection members 28 are shown in broken lines.

FIG. 9A is a top view of the arms 24 and the deflection member 28 positioned on the bottom plate 300 with arms 24 bracketing the male connection elements 302 and overlaying the aperture 304 through the bottom plate 300. In FIG. 9A, the arms 24 are in an un-deflected state, that is, no force or pressure is applied to the deflection members 28 to generate deflection of the arms 24. FIG. 9B is a top view of the arms 24 and the deflection member 28 positioned on the bottom plate 300 and in a deflected configuration caused by applying force or pressure to the deflection members 28 to generate deflection of the arms 24. As can be seen in FIG. 9B, the male connection elements 302 limit the inward travel of the deflection members 28. The male connection elements 302 also limit the amount of force that can be applied to the arms 24.

FIG. 10A is a side view of an exemplary connecter 10 illustrating the cap 12, the bottom plate 300, the conduit 32 and the deflection member 28 as well as other components that are not shown (e.g., the arms 24 and the male connection elements and female connection elements, etc.) in an assembled state. FIG. 10B is a top view of the connector 10 of FIG. 10A illustrating the top surface 14 of the cap 12, the conduit 32, and the deflection members 28. In this illustration, the deflection members are in an un-deflected state. That is, no force or pressure is applied to the deflection members 28 to generate deflection of the arms 24. FIG. 10C is a top view of the connector 10 of FIG. 10A illustrating the top surface 14 of the cap 12, the conduit 32, and the deflection members 28. In this illustration, the deflection members are in a deflected state. That is, force or pressure is applied to the deflection members 28 causing them to be displaced inwardly (i.e., towards the circumferential region 22 of the cap 12) to generate deflection of the arms 24.

FIG. 11A is a bottom view of an exemplary connector 10 in position and engaged with a section of an exemplary circular hub 40 of an enteral feeding device 36. FIG. 11A illustrates the cap 12 with two deflection member 28a and 28b, two resilient components 306, and two arms 24 engaged with the annular recess of the circular hub 40. A first end 308 of each arm 24 is connected to a pivot 310 that allows the arm 24 to move at the pivot 310 (e.g., rotate) a limited amount in a direction that is parallel to the bottom plane. The second end 312 of the arm is free to move within a pocket 314 (e.g., a slotted recess) created within the respective deflection member 28b (i.e., the deflection member 28b at the second end 312 of the arm 24) or between the respective deflection member 28b and the bottom surface 15 of the cap 12. The deflection member 28a nearest the pivots 310 is in contact with at least one arm 24. This deflection member 28a is configured to contact the first end 308 of the arm 24 and move the second end 312 of the arm 24 towards the periphery 22 and out of the annular recess of the hub 40. The resilient component 306 reversibly compresses to allow movement of the arm 24 towards the periphery 22 when the deflection member 28a is pressed (or both deflection members 28a and 28b are pressed) inwardly towards the circular hub 40, but returns the arms 24 to the position to engage the recess of the circular hub 40 in the absence of a force imparted by the deflection member 28 (or by the downwards force that can be applied to the cap when seating the cap on the hub). The resilient component 306 may be one or more flexible, resilient foams, compressible elastomeric materials, elastic bands or strips, compressible bladders, metal or plastic strips, springs (e.g., coil compression springs, cantilever spring, volute or secateur springs, conical springs) and the like as well as combinations thereof.

Referring again to FIG. 5 of the drawings, each arm 24 is configured to releasably engage the annular recess defined in the side surface of the circular hub. Desirably, each arm 24 may have a top surface 110. The top surface 110 is configured to lie adjacent an underside (not shown) of rim, rib, lip, or flange structure 48 of the annular recess 46. Each arm may also have a bottom surface 112. Desirably, a portion of the bottom surface 112 may have a bevel 114. The bevel 114 can be adjusted to provide an angle sufficient to allow for easier attachment to the hub when the connector 10 is pressed downward against and onto the circular hub 40. The presence of the bevel 114 helps avoid applying a force that creates discomfort and causes irritation to the sensitive stoma site. Referring to FIGS. 14A to 14D of the drawings, there is shown in side cross-sectional view (not to scale), illustrations of various exemplary cross-sectional shape configurations that may be utilized with the arms 24 of the present invention to engage the recess of the circular hub (not to scale). As seen in FIG. 14A, the arms 24 may be in the form of a parallelogram having a top surface 110 and a bottom surface 112 (or the arms may have sides that are not parallel and define angles that may be less than or greater than 180 degrees). Desirably, the sides may slope as seen in FIG. 14A to provide an angle sufficient to allow for easier attachment to the hub when the connector 10 is pressed downward onto the top surface 42 of the circular hub 40 so the connector can engage the recess 46 defined in the vertical side surfaces 44 by the rim, rib, lip, or flange structure 48. Generally speaking, FIG. 14A illustrates a generally rhombus or rhomboid cross-section. FIG. 14B is an illustration showing the arms 24 having a triangular cross-sectional shape having a top surface 110. FIG. 14C is an illustration showing the arms 24 having a generally trapezoid cross-sectional shape with a top surface 110, a bottom surface 112 and a bevel 114. It is contemplated that the arms 24 may have trapezium cross-section in which no sides are parallel. It is also contemplated that the arms may have cross-sections characterized by combinations of linear and non-linear sides. As an example, FIG. 14D is an illustration showing the arms 24 having a generally circular cross-sectional shape. It is contemplated that the arms may have semi-circular, partially circular, semi-oval, partially oval or other combinations of linear and non-linear sides such that the sides can be adjusted to provide an angle or surface configured to allow for easier attachment to the hub when the connector 10 is pressed downward against and onto the circular hub 40.

As previously noted, the connector includes a cap 12. The cap 12 may have a clamshell or bowl shape. A portion of the cap 12 may be joined to an optional bottom plate 300 (as illustrated in FIGS. 6A and 6B) or the cap 12 may be formed as a unitary element such that the cap 12 and bottom plate 300 are unitary or monolithic. In an aspect of the invention, all the various structural members of connector 10 may be formed separately and subsequently joined together by techniques involving adhesion, fusion, overmolding, etc. alone or in combination.

Referring now to FIG. 13, there is shown a bottom view of an exemplary connector 10 from FIG. 1 illustrating the bottom surface 16 of the cap 12. In this illustration, the optional motion stabilizers 80 are located near the periphery 22. As can be seen in FIG. 9, the arms 24 span at least two portions within the circumferential region 20 so they are positioned to releasably engage the annular recess 46 in the circular hub 40. In addition, the arms 24 may be positioned directly below and aligned with the ports 50 to allow visual inspection of the engagement with the circular hub.

According to the invention, the connector 10 is "rotatably coupled" to the circular hub 40. That is, the connector freely rotates completely about the circular hub when coupled to the base of the enteral feeding device. The connector is configured to freely rotate completely around the hub without passing through a position or location where the connector encounters a feature such as a keyway, a groove, a slot or the like which would allow the connector to be inadvertently disengaged and/or without encountering a feature such as a stop, detent or the like that would inhibit or prevent rotation completely around the hub thereby causing the enteral feeding device to twist. Desirably, the connector is configured to rotate completely around the hub multiple times while providing little or no resistance so that the enteral feeding device does not twist or turn.

The present invention also encompasses an enteral feeding assembly. The enteral feeding assembly is composed of: (i) an enteral feeding device having a base and including a catheter with a lumen positioned through the base, the base having a circular hub having a radius, a top surface, a side surface and an annular recess defined in the side surface; and (ii) an extension set with a connector for rotatably coupling to the base of an enteral feeding device. The connector is as generally described above.

The present invention further encompasses a feeding extension set. The feeding extension set includes a medical supply tube and a connector for use with an enteral feeding device having a circular hub. The connector is as generally described above.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

I claim:

1. A connector for coupling a medical fluid supply tube to the head of a catheter device with a circular hub having an annular recess defined in a side surface of the circular hub, the connector comprising:
   a cap having a top surface, a bottom surface, and a circumferential region defining a bottom plane and a periphery;
   at least two arms substantially parallel to the bottom plane, each arm spanning across the bottom plane between two radially opposite recessed portions defined within the circumferential region so it is positioned to releasably engage the annular recess;
   a deflection member disposed at each of the recessed portions within the circumferential region and connected directly to both of the arms to deflect the arms, the deflection member being accessible from the top surface;
   the deflection members connected to each other by only the two arms;
   wherein the connector is free to rotate completely about the circular hub, and wherein the connector decouples from the circular hub by pressing at least one deflection member radially into its respective recessed portion towards the radially opposite recessed portion in the circumferential region to reversibly deflect at least one arm between the two recessed portions of the circumferential region towards the periphery within the cap in order to disengage from the annular recess.

2. The connector of claim 1, wherein at least one arm comprises a resilient material.

3. The connection of claim 1, wherein the connector is coupled to the hub by positioning the connector on the hub and pressing the top surface of the cap to move the bottom surface of the cap towards the hub until the arms engage the annular recess.

4. The connector of claim 1, wherein the cap has a port located above at least one arm to permit visual inspection of engagement between the arm and the annular recess.

5. The connector of claim 1, wherein each arm is spatially displaced when a force of between about 2 Newtons and about 14 Newtons is applied to the at least one deflection member.

6. The connector of claim 1, further comprising motion limiters to limit the pitch of the connector.

7. The connector of claim 1, wherein each arm has a top surface configured to releasably engage the annular recess and a bottom surface that defines a bevel.

8. The connector of claim 1, further comprising a conduit defining a fluid pathway through the connector, the conduit configured to supply a liquid to a passageway defined by the catheter device.

9. An enteral feeding assembly comprising:
   an enteral feeding device having a base, at least one passageway positioned through the base, at least one circular hub on the base, the circular hub having a radius, a top surface, a side surface and an annular recess defined in the side surface; and
   a feeding extension set including a connector according to claim 1, wherein the connector allows for fluid communication between the feeding extension set and at least one passageway of the enteral feeding device.

10. An extension set connector for coupling to a circular hub of an enteral feeding device, the circular hub having a radius, a top surface, a side surface, and an annular recess defined in the side surface, the connector comprising:
    a cap having a top surface, a bottom surface, and a circumferential region defining a bottom plane and a periphery;
    at least two arms, each arm spanning across the bottom plane between radially opposite recessed portions defined with the circumferential region so that each arm is positioned to releasably engage the annular recess;
    a deflection member disposed at each of the recessed portions within the circumferential region and connected directly to both of the arms to deflect the arms, the deflection member being accessible from the top surface;
    the deflection members connected to each other by only the two arms;
    a conduit defining a fluid pathway through the connector, the conduit configured to supply a feeding solution to a lumen of the enteral feeding device,
    wherein the connector is free to rotate completely about the circular hub, and wherein the connector decouples from the circular hub by pressing at least one deflection member radially into its respective recessed portion towards the radially opposite recessed portion in the circumferential region to reversibly deflect at least one arm between the two recessed portions of the circumferential region towards the periphery within the cap in order to disengage from the annular recess.

11. The connector of claim 10, wherein at least one arm is resilient.

12. The connector of claim 10, wherein the cap has a port located above at least one arm to permit visual inspection of engagement between the arm and the annular recess defined in the side surface of the circular hub.

13. The connector of claim 10, wherein each arm has a top surface configured to releasably engage the annular recess and a bottom surface that defines a bevel.

14. A feeding extension set, comprising:
    a tube; and
    a connector in fluid communication with the tube, the connector configured for rotatably coupling the tube to an enteral feeding device that has a circular hub, the connector including:
    a cap having a top surface, a bottom surface, and a circumferential region with a periphery;
    at least two arms, each arm spanning across the bottom surface between radially opposite recessed portions defined in the circumferential region so it is positioned to releasably engage an annular recess defined in a side surface of the circular hub;

a deflection member disposed at each of the recessed portions within the circumferential region and connected directly to both of the arms to deflect the arms, the deflection member being accessible from the top surface;

the deflection members connected to each other by only the two arms;

a conduit defining a fluid pathway through the connector, the conduit configured to supply a feeding solution to a passageway of the enteral feeding device, wherein the connector is coupled to the circular hub by the arms that engage the annular recess such that the connector is free to rotate completely about the circular hub, and wherein the connector decouples from the circular hub by pressing at least one deflection member radially into the recessed portion towards the radially opposite recessed portion in the circumferential region to reversibly deflect the arm relative to the circumferential region in order to disengage from the annular recess.

* * * * *